United States Patent [19]
Yale

[11] 3,965,100
[45] June 22, 1976

[54] 2,3-DIHYDROCYCLOPENTA[D-]PYRIDO[1,2-a]PYRIMIDIN-10(1H)-ONE AND ITS DERIVATIVES

[75] Inventor: Harry L. Yale, New Brunswick, N.J.

[73] Assignee: E. R. Squibb & Sons, Inc., Princeton, N.J.

[22] Filed: Feb. 26, 1975

[21] Appl. No.: 553,341

[52] U.S. Cl.................... 260/251 A; 260/256.4 F; 260/295.5 R; 260/296 AE; 260/296 R; 424/251
[51] Int. Cl.² ........................................ C07D 471/04
[58] Field of Search ................. 260/251 A, 256.4 F

[56] References Cited
OTHER PUBLICATIONS
Maillard et al., Chemical Abstracts, vol. 68, 12949h (1968).
Brown et al. Chemical Abstacts, vol. 75, 48839f (1971).

Primary Examiner—Nicholas S. Rizzo
Assistant Examiner—Diana G. Rivers
Attorney, Agent, or Firm—Lawrence Levinson; Merle J. Smith; Burton Rodney

[57] ABSTRACT

Compounds of the formula

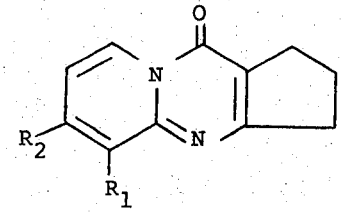

are provided which are useful as central nervous system depressants.

10 Claims, No Drawings

2,3-DIHYDROCYCLOPENTA(D)PYRIDO(1,2-PYRIMIDIN-10(1H)-ONE AND ITS DERIVATIVES

The present invention relates to 2,3-dihydrocyclopenta[d]pyrido[1,2-a]pyrimidin-10(1H)-one and its derivatives and to a method for preparing the same, as well as to a method for tranquilizing the central nervous system employing the above derivatives.

The 2,3-dihydrocyclopenta[d]pyrido[1,2-a]pyrimidin-10(1H)-one and its derivatives in accordance with the invention have the formula

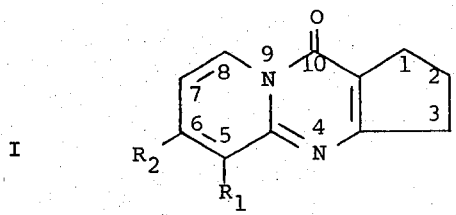

I wherein $R_1$ and $R_2$ are the same or different and can be hydrogen, lower alkyl, aryl, aralkyl, carboxyl or halo. Furthermore, $R_1$ or $R_2$ can be hydroxyl, lower alkoxy, aralkoxy, carboalkoxy, or carboxamido, in which case the other of $R_2$ and $R_1$ must be hydrogen.

Preferred are those compounds wherein $R_2$ is hydrogen; more preferred are those compounds wherein $R_2$ is hydrogen and $R_1$ is alkyl, hydroxyl, carboxyl, or aralkoxy.

The term "alkyl" as used herein refers to straight or branched chain alkyl groups having 1 to 6 carbons, such as methyl, ethyl, propyl, isopropyl, butyl, s-butyl, t-butyl, amyl and heptyl. Those alkyl groups having 1 to 3 carbons are preferred.

The term "alkoxy" as used herein refers to groups having the formula RO— wherein R is an alkyl group as defined above.

The term "aryl" as used herein refers to monocyclic or bicyclic aromatic ring systems substituted with an alkyl group halo, alkoxy, or trifluoromethyl group.

The terms "aralkyl" and "aralkoxy" refer to an alkyl group or alkoxy group as defined above including an aryl substituent as defined above.

The term "carboalkoxy" as used herein refers to groups having the formula $RO_2C$— wherein R is an alkyl group as defined above.

The term "carboamido" as used herein refers to groups having the formula R'NHCO— wherein R' is hydrogen or lower alkyl.

The term "halo" or "halogen" as used herein refers to fluorine, chlorine, bromine and iodine, with chlorine and bromine being preferred.

The compounds of formula I of the invention wherein at least one of $R_1$ and $R_2$ is hydrogen, carboxy, alkyl, hydroxy, aryl, alkoxy, and aralkyl can be prepared by reacting the appropriately substituted 2-aminopyridine of the formula II

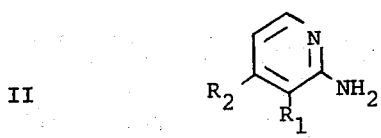

II with an ester of cyclopentanone-2-carboxylic acid of the formula III; an acidic catalyst like concentrated sulfuric acid, methanesulfonic acid, p-toluenesulfonic acid, or a resin-bonded catalyst like mixed bed sulfonic acid resin, for example, IR-4B (Rohm and Haas), may be employed.

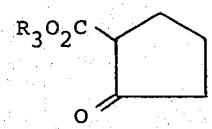

III wherein $R_3$ is methyl or ethyl.

Reaction conditions are not critical. However, the above reaction may be carried out in an organic solvent, such as a monoalkyl ether of ethylene glycol, for example, ethylene glycol monomethyl ether or monoethyl ether, or in an aromatic solvent having a boiling point above 150°C, such as, diethylbenzene, cumene, cymene and the like; however where the reactant of formula II is an aminonicotinic acid or an aminoisonicotinic acid with or without other substituents, no solvent is necessary, and the ester of the cyclopentanone-2-carboxylic acid (III) is employed in excess (over 3 moles per mole of the formula II reactant). The above reaction may be carried out at a temperature ranging from about 120° to about 210°C and preferably from about 140° to about 195°C, for a period of from about 0.5 hour to about 48 hours and preferably from about 1 hour to about 24 hours.

The substituted 2-aminopyridine (II) will generally be employed in a molar ratio to the ester of the cyclopentanone-2-carboxylic acid in a range of from about 1:2 to about 1:6 and preferably from about 1:2 to about 1:4.

Compounds of formula I wherein at least one of $R_1$ and $R_2$ is carboalkoxy may be prepared by esterification of an acid of formula I of the invention, that is wherein at least one of $R_1$ or $R_2$ is a carboxyl group, with a lower alkanol in the presence of a mineral acid, such as sulfuric acid, employing conventional techniques.

Compounds of formula I wherein one of $R_1$ and $R_2$ is aralkoxy or alkoxy may be prepared by reacting a compound of formula I wherein at least one of $R_1$ and $R_2$ is hydroxy with an aralkyl halide or alkyl halide, respectively, in the presence of an anhydrous base, such as an alkali metal carbonate or bicarbonate, and an organic solvent, such as ethyl methyl ketone, or alternatively, by means of sodium hydride and the halide and an organic solvent like N,N-dimethylformamide, or sodium hydroxide, the halide, and an aromatic solvent like xylene, with or without copper bronze as a catalyst.

In yet an alternative method for preparing compounds of formula I wherein one of $R_1$ and $R_2$ is alkoxy or aralkoxy, the 2-aminopyridine of formula IIa

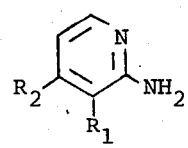

IIa wherein $R_1$ or $R_2$ is hydroxy is treated with an alkyl halide or an aralkyl halide according to the procedure of Yale and Pluscec, J. Org. Chem. 36, 3238 (1971) to give compounds of the formula IIb IIb 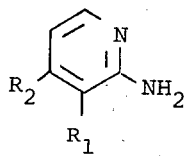

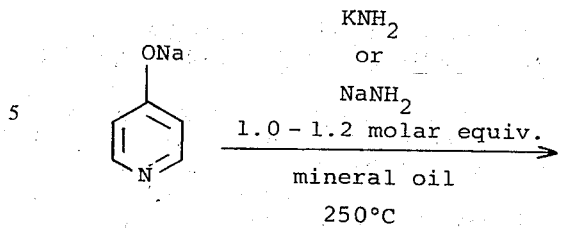

wherein $R_1$ or $R_2$ is alkoxy or aralkoxy and the other of $R_2$ and $R_1$ is hydrogen or carboxyl and the formula IIb compound is reacted with the ester of cyclopentanone-2-carboxylic acid of formula III as described above.

Compounds of formula I wherein one of $R_1$ and $R_2$ is carboamido or N-lower alkylcarboxamido may be prepared by reacting a compound of the invention of formula I wherein $R_1$ or $R_2$ is carboalkoxy with ammonia or an N-loweralkylamine in the presence of an alcohol solvent, such as methanol.

All of the starting materials of formulae II and III are known or easily prepared employing conventional procedures. Thus, where the starting material of formula II has the structure

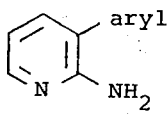

IV

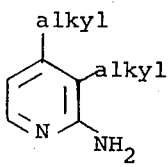

V wherein alkyl is ethyl or a higher alkyl, the formulae IV and V compounds may be prepared by the Chichibabin reaction of a 2-aryl substituted pyridine or a 2,3-dialkyl substituted pyridine, respectively, with sodium amide.

2-Aminonicotinic acid starting materials of the structure

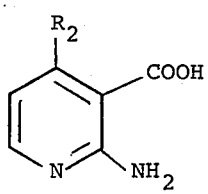

can be prepared from the corresponding quinoline derivative according to the procedure of E. Späth and G. Koller, *Chem. Ber.*, 56, 2454 (1923).

2-Amino-4-hydroxypyridine can be prepared by the Chichibabin reaction as outlined below and in accordance with the procedure disclosed by Bojarska-Dahlig and Nantka-Namirski, *Roczniki Chem.*, 30, 461 (1956).

2-Amino-alkoxy or aralkoxy substituted pyridines can be prepared, in addition, by the methods described in "Pyridine and Derivatives", Vol. 14 of Wiley-Interscience Series on "Heterocyclic Compounds", Part 3, page 571.

The compounds of the invention of formula I can be converted, using procedures well known in the art, into their pharmaceutically acceptable acid-addition salts. Illustrative of the salts contemplated for use in this invention are the hydrohalides (e.g., the hydrochloride and hydrobromide), sulfate, nitrate, tartrate, phosphate, maleate, fumarate, citrate, succinate, methanesulfonate, benzenesulfonate, toluenesulfonate, and the like.

The compounds of formula I, and the pharmaceutically acceptable acid-addition salts thereof, are useful in mammalian species such as rats, dogs, monkeys and others, as central nervous system depressants, and can be used as tranquilizers for the relief of anxiety and tension states in the same manner as triflupromazine and fluphenazine. For this purpose, these compounds can be incorporated in a conventional dosage form such as tablet, capsule, injectable or the like, along with the necessary carrier material, excipient, lubricant, buffer or the like, for oral or parenteral administration in single or divided doses of about 1 to 35 mg/kg/day, and preferably about 5 to 15 mg/kg, two to four times daily.

The following examples represent preferred embodiments of this invention. All temperatures are expressed in degrees Centigrade.

EXAMPLE 1

2,3-Dihydro-5-hydroxycyclopenta[d]pyrido[1,2-a]pyrimidin-10(1H)-one

A solution of 22.0 g of 2-amino-3-pyridinol, 62.4 g of ethyl cyclopentanone-2-carboxylate, and 200 ml of diethylbenzene is stirred and heated by means of oil bath maintained at ca. 150° for 1 hour, then gradually raised to 195°, and kept at 195° for 1 hour. Some tarry products are formed; hence the diethylbenzene solution is decanted from the tar and the diethylbenzene solution concentrated in vacuo. The residue, 29.8 g is recrystallized from 1400 ml of Skellysolve E to give 22.4 g of product, mp 136°–142°.

EXAMPLE 2

2,3-Dihydro-5-(phenylmethoxy)cyclopenta[d-]pyrido[1,2-a]pyrimidin-10(1H)-one A suspension of 2,3-dihydro-5-hydroxycyclopenta[d-]pyrido[1,2-a]pyrimidin-10(1H)-one prepared as described in Example 1, (6.1 g), 9.9 g of anhydrous potassium bicarbonate, 6.2 g of benzyl bromide, and 300 ml of ethyl methyl ketone is stirred and slowly heated to reflux. Stirring and heating under reflux is continued for 18 hours. The hot solution is filtered to remove inorganic salts and the ethyl methyl ketone filtrate is concentrated in vacuo to give 10.0 g of crude product; this, when recrystallized from 1000 ml of cyclohexane, and the crystalline solid dried at 78° for 2 hours, gives 6.0 g of product, mp 150°–152°.

EXAMPLE 3

2,3-Dihydro-5-methylcyclopenta[d]pyrido[1,2-a]pyrimidin-10(1H)-one

A mixture of 10.8 g of 2-amino-3-picoline, 31.2 g of ethyl cyclopentanone-2-carboxylate, and 250 ml of ethylene glycol monomethyl ether is stirred and heated under reflux for 40 hours. The solution is concentrated as far as possible on a rotary evaporator. The residual oil crystallizes and is filtered with suction to give 14.15 g of air-dried solid. This is recrystallized from 425 ml of cyclohexane to give 11.3 g of product, after drying at 78°. The melting point is 100°–102°.

Further concentration of the filtrate from the 14.15 g. gives additional product. The overall yield of recystallized product is 12.0 g.

EXAMPLE 4

1,2,3,10-Tetrahydro-10-oxocyclopenta[d]pyrido[1,2-a]pyrimidine-5-carboxylic acid A mixture of 5.0 g of 2-aminonicotinic acid, 0.4 g. p-toluenesulfonic acid, and 25 ml of ethyl cyclopentanone-2-carboxylate is stirred magnetically and immersed in an oil bath preheated to 125°. The temperature of the oil bath is gradually raised and reaches 170° in 23 minutes. A clear solution occurs in 55 minutes when the oil bath temperature reaches 178° and 4.0 ml of distillate is collected in a Dean-Stark trap. The product crystallizes from the cooled reaction mixture. The filtered, air-dried product weighs 6.2 g., m.p. 187°–192°. Recrystallization from 100 ml of toluene gives 4.91 g of product, m.p. 189°–193°.

EXAMPLE 5

1,2,3,10-Tetrahydro-10-oxocyclopenta[d]pyrido[1,2-a]pyrimidine-5-carboxylic acid, methyl ester A suspension of 7.0 g. of the product from Example 4, 500 ml of absolute methanol, and 18.4 g. of concentrated sulfuric acid is stirred and heated under reflux for 48 hours. A clear solution forms after that heating period. The solution is concentrated in vacuo, the residue is cooled, dissolved in 200 ml of ether, and the ether solution is washed with saturated aqueous sodium bicarbonate until the washings remain at pH 7.6. The ether solution is dried an concentrated to give the named compound.

EXAMPLE 6

1,2,3,10-Tetrahydro-10-oxocyclopenta[d]pyrido[1,2-a]pyrimidine-5-carboxamide A solution of 2.44 g. of the product from Example 5 in 50 ml of methanol is cooled to −10° and a stream of dry ammonia gas is introduced. When the increase in weight of the absorbed ammonia is 3.4 g., the addition is stopped, the flask is sealed, and kept at 20°–25° for 24 hours. The solid that separates is filtered and recrystallized from 2-propanol to give the named compound as colorless needles.

EXAMPLE 7

2,3-Dihydro-5,6-dimethylcyclopenta[d]pyrido[1,2-a]pyrimidin-10(1H)-one

A solution of 24.4 g. of 2-amino-3,4-dimethylpyridine, 62.4 g. of methyl cyclopentanone-2-carboxylate and 250 ml of ethylene glycol monomethyl ether is stirred and heated under reflux for 40 hours. Workup as in Example 3 gives 28.3 g. of the named product as colorless plates after recrystallization from cyclohexane.

EXAMPLE 8

2,3-Dihydro-6-phenylcyclopenta[d]pyrido[1,2-a]pyrimidin-10(1H)-one

A mixture of 17.0 g. of 2-amino-4-phenylpyridine and 31.2 g. of ethyl cyclopentane-2-carboxylate is heated at an internal temperature of 160°–165° for 4 hours. During this time ethanol distils from the reaction mixture and is collected in a Dean-Stark trap. During the 4 hours of heating, about 5.5 ml of distillate is collected. When the reaction mixture is allowed to cool, a crystalline solid separates. The mixture is cooled to 0° and the solid filtered. Recrystallization from cyclohexane gives 24.7 g. of 2,3-dihydro-6-phenylcyclopenta[d]pyrido[1,2-a]pyrimidin-10(1H)-one.

EXAMPLE 9

2,3-Dihydro-6-chlorocyclopenta[d]pyrido[1,2-a]pyrimidin-10(1H)-one

By substituting 25.7 g. of 2-amino-4-chloropyridine for the 24.4 g. of 2-amino-3,4-dimethylpyridine in Example 7, there is obtained 30.3 g. of the named compound as colorless needles after recrystallization from cyclohexane.

EXAMPLE 10

2,3-Dihydro-6-n-pentylcyclopenta[d]pyrido[1,2-a]pyrimidin-10(1H)-one

By substituting 32.8 g. of 2-amino-4-n-pentylpyridine for the 2-amino-3,4-dimethylpyridine in Example 7, there is obtained 34.7 g of 2,3-dihydro-6-n-pentylcyclopenta[d]pyrido[1,2-a]pyrimidin-10(1H)-one as colorless plates after recrystallization from heptane.

EXAMPLE 11

2,3-Dihydro-6-bromocyclopenta[d]pyrido[1,2-a]pyrimidin-10(1H)-one

By substituting 2-amino-4-bromopyridine for the 2-amino-3,4-dimethylpyridine in Example 7, there is obtained the named compound.

EXAMPLE 12

2,3-Dihydro-5-bromocyclopenta[d]pyrido[1,2-a]pyrimidin-10(1H)-one

By substituting 2-amino-3-bromopyrimidine for the 2-amino-3,4-dimethylpyridine in Example 7, there is obtained the named compound.

EXAMPLE 13

2,3-Dihydro-5-chlorocyclopenta[d]pyrido[1,2-a]pyrimidin-10(1H)-one

By substituting 2-amino-3-chloropyridine for the 2-amino-3,4-dimethylpyridine in Example 7, there is obtained the named compound.

EXAMPLE 14

2,3-Dihydro-5,6-dibromocyclopenta[d]pyrido[1,2-a]pyrimidin-10(1H)-one

By substituting 2-amino-3,4-dibromopyridine for the 2-amino-3,4-dimethylpyridine in Example 7, there is obtained the named compound.

EXAMPLE 15

2,3-Dihydro-5-phenylcyclopenta[d]pyrido[1,2-a]pyrimidin-10(1H)-one

2-Amino-3-phenylpyridine is prepared by reacting 46.5 g. 3-phenylpyridine with 11.7 g. of sodium amide at a temperature of 250° in the presence of mineral oil. The 2-amino-3-phenylpyridine that is formed is purifed by distillation and is substituted for the 2-amino-4-phenylpyridine in Example 8 to obtain the named compound.

EXAMPLE 16

2,3-Dihydro-5,6-diethylcyclopenta[d]pyrido[1,2-a]pyrimidin-10(1H)-one

2-Amino-3,4-diethylpyridine is prepared by reacting 40.5 g. 3,4-diethylpyridine with 11.7 g sodium amide at a temperature of 250° in the presence of paraffin oil. The so-formed 2-amino-3,4-diethylpyridine is purified by distillation and is substituted for the 2-amino-3,4-dimethylpyridine in Example 7 to obtain the named compound.

EXAMPLE 17

1,2,3,10-Tetrahydro-6-methyl-10-oxocyclopenta[d]pyrido[1,2-a]pyrimidine-5-carboxylic acid By substituting 2-amino-4-methylnicotinic acid for the 2-aminonicotinic acid in Example 4, there is obtained the named compound.

EXAMPLE 18

1,2,3,10-Tetrahydro-6-chloro-10-oxocyclopenta[d]pyrido[1,2-a]pyrimidine-5-carboxylic acid by substituting 2-amino-4-chloronicotinic acid for the 2-aminonicotinic acid in Example 4, there is obtained the named compound.

EXAMPLE 19

1,2,3,10-Tetrahydro-10-oxocyclopenta[d]pyrido[1,2-a]pyrimidine-6-carboxylic acid By substituting 2-aminoisonicotinic acid for the 2-aminonicotinic acid in Example 4, there is obtained the named compound.

EXAMPLE 20

1,2,3,10-Tetrahydro-6-(m-tolyl)-10-oxocyclopenta[d]pyrido[1,2-a]pyrimidine-5-carboxylic acid By substituting 2-amino-4-(m-tolyl)nicotinic acid for the 2-aminonicotinic acid in Example 4, there is obtained the named compound.

EXAMPLE 21

1,2,3,10-Tetrahydro-6-(o-ethoxyphenyl)-10-oxocyclopenta[d]pyrido[1,2-a]pyrimidine-5-carboxylic acid By substituting 2-amino-4-(o-ethoxyphenyl)nicotinic acid for the 2-aminonicotinic acid in Example 4, there is obtained the named compound.

EXAMPLE 22

1,2,3,10-Tetrahydro-6-ethoxy-10-oxocyclopenta[d]pyrido[1,2-a]pyrimidine-5-carboxylic acid By substituting 2-amino-4-ethoxynicotinic acid (prepared by reaction of the 2-amino-4-hydroxynicotinic acid with ethyl bromide in accordance with the procedure of Yale and Pluscec, supra.) for the 2-aminonicotinic acid in Example 4, there is obtained the named compound.

EXAMPLE 23

2,3-Dihydro-5,6-diphenylcyclopenta[d]pyrido[1,2-a]pyrimidin-10(1H)-one

By substituting 2-amino-3,4-diphenylpyridine for the 2-amino-4-phenylpyridine in Example 8, there is obtained the named compound.

EXAMPLE 24

2,3-Dihydro-5-t-butylcyclopenta[d]pyrido[1,2-a]pyrimidin-10(1H)-one

By sutstituting 2-amino-3-t-butylpyridine for the 2-amino-3-picoline in Example 3, there is obtained the named compound.

EXAMPLE 25

2,3-Dihydro-6-methylcyclopenta[d]pyrido[1,2-a]pyrimidin-10(1H)-one

By substituting 2-amino-4-picoline for the 2-amino-3-picoline in Example 3, there is obtained the named compound.

EXAMPLE 26

2,3-Dihydro-6-ethylcyclopenta[d]pyrido[1,2-a]pyrimidin-10(1H)-one

By substituting 2-amino-4-ethylpyridine for the 2-amino-3-picoline in Example 3, there is obtained the named compound.

EXAMPLE 27

2,3-Dihydro-6-(n-pentyl)cyclopenta[d]pyrido[1,2-a]pyrimidin-10(1H)-one

By substituting 2-amino-4-(n-pentyl)pyridine for the 2-amino-3-picoline in Example 3, there is obtained the named compound.

EXAMPLE 28

2,3-Dihydro-6-(2-methylbutyl)cyclopenta[d-]pyrido[1,2-a]pyrimidin-10(1H)-one

By substituting 2-amino-4-(2-methylbutyl)pyridine for the 2-amino-3-picoline in Example 3, there is obtained the named compound.

EXAMPLE 29

2,3-Dihydro-6-(3-methylbutyl)cyclopenta[d-]pyrido[1,2-a[pyrimidin-10(1H)-one

By substituting 2-amino-4-(3-methylbutyl)pyridine for the 2-amino-3-picoline in Example 3, there is obtained the named compound.

EXAMPLE 30

2,3-Dihydro-6-benzylcyclopenta[d]pyrido[1,2-a]pyrimidin-10(1H)-one

By substituting 2-amino-4-benzylpyridine for the 2-amino-3-picoline in Example 3, there is obtained the named compound.

EXAMPLE 31

2,3-Dihydro-5-(phenylmethoxy)cyclopenta[d-]pyrido[1,2-a]pyrimidin-10(1H)-one

To a solution of 6.1 g. of 2,3-dihydro-5-hydroxycyclopenta[d]pyrido[1,2-a]pyrimidin-10(1H)-one in 100 ml of N,N-dimethylformamide is added, portionwise, a total of 1.6 g of a 50% dispersion of sodium hydride in mineral oil. A yellow precipitate of the sodium salt separates. The mixture is allowed to stir for 0.5 hour at room temperature, and then 6.2 g. of benzyl bromide dissolved in 25 ml of N,N-dimethylformamide is added, dropwise, followed by 100 mg. of copper bronze powder. The mixture is stirred and heated to 100°–110° and kept at that temperature for 2 hours. The hot solution is filtered, concentrated in vacuo, and the solid residue recrystallized from cyclohexane to give 7.2 g. of product, m.p. 150°–152°.

EXAMPLE 32

2,3-Dihydro-6-(n-butoxy)cyclopenta[d]pyrido[1,2-a]pyrimidin-10(1H)-one

By substituting 4.6 g. of n-butyl bromide in Example 31 for the benzyl bromide employed therein, there is obtained the named product as a colorless crystalline solid.

EXAMPLE 33

2,3-Dihydro-5-(phenylmethoxy)cyclopenta[d-]pyrido[1,2-a]pyrimidin-10(1H)-one

A stirred mixture of 6.1 g. of 2,3-dihydro-5-hydroxycyclopenta[d]pyrido[1,2-a]pyrimidin-10(1H)-one, 1.40 g. of powdered sodium hydroxide, 100 ml of xylene, 100 mg of copper bronze, and 6.2 g. of benzyl bromide are stirred and heated under reflux for 12 hours, and filtered hot. From the filtrate, on cooling, the product crystallizes. It is filtered and recrystallized from xylene to give 6.3 g. of product, m.p. 150°–152°.

EXAMPLE 34

2,3-Dihydro-5-methoxycyclopenta[d]pyrido[1,2-a]pyrimidin-10(1H)-one

By substituting 2-amino-3-methoxypyridine for the 2-amino-3,4-dimethylpyridine in Example 7, there is obtained the named compound.

EXAMPLE 35

2,3-Dihydro-5-ethoxycyclopenta[d]pyrido[1,2-a]pyrimidin-10(1H)-one

By substituting 2-amino-3-ethoxypyridine for the 2-amino-3,4-dimethylpyridine in Example 7, there is obtained the named compound.

EXAMPLE 36

2,3-Dihydro-6-methoxycyclopenta[d]pyrido[1,2-a]pyrimidin-10(1H)-one

By substituting 2-amino-4-methoxypyridine for the 2-amino-3,4-dimethylpyridine in Example 7, there is obtained the named compound.

EXAMPLE 37

2,3-Dihydro-6-ethoxycyclopenta[d]pyrido[1,2-a]pyrimidin-10(1H)-one

By substituting 2-amino-4-ethoxypyridine for the 2-amino-3,4-dimethylpyridine in Example 7, there is obtained the named compound.

EXAMPLE 38

2,3-Dihydro-6-n-propylcyclopenta[d]pyrido[1,2-a]pyrimidin-10(1H)-one

By substituting 2-amino-4-n-propylpyridine for the 2-amino-3,4-dimethylpyridine in Example 7, there is obtained the named compound.

EXAMPLE 39

2,3-Dihydro-6-isopropylcyclopenta[d]pyrido[1,2-a]pyrimidin-10(1H)-one

By substituting 2-amino-4-isopropylpyridine for the 2-amino-3,4-dimethylpyridine in Example 7, there is obtained the named compound.

EXAMPLE 40

2,3-Dihydro-6-n-pentylcyclopenta[d]pyrido[1,2-a]pyrimidin-10(1H)-one

By substituting 2-amino-4-(n-pentyl)pyridine for the 2-amino-3,4-dimethylpyridine in Example 7, there is obtained the named compound.

EXAMPLE 41

2,3-Dihydro-6-(3-methylbutyl)cyclopenta[d-]pyrido[1,2-a]-pyrimidin-10(1H)-one

By substituting 2-amino-4-(3-methylbutyl)pyridine for the 2-amino-3,4-dimethylpyridine in Example 7, there is obtained the named compound.

EXAMPLE 42

2,3-Dihydro-6-n-hexylcyclopenta[d]pyrido[1,2-a[pyrimidin-10(1H)-one

By substituting 2-amino-4-n-hexylpyridine for the 2-amino-3,4-dimethylpyridine in Example 7, there is obtained the named compound.

EXAMPLE 43

2,3-Dihydro-5-methylcyclopenta[d]pyrido[1,2-a]pyrimidin-10(1H)-one, salt with maleic acid (1:2)

To a solution of 4.0 g. of 2,3-dihydro-5-methylcyclopenta[d]pyrido[1,2-a]pyrimidin-10(1H)-one in 20 ml of acetonitrile is added a solution of 2.32 g. of maleic acid in 25 ml of acetonitrile. Both solutions are heated to the boiling point before mixing. On cooling, the salt with maleic acid separates as a pale yellow crystalline solid. The solid is filtered and recrystallized from 2-propanol to give the named compound.

EXAMPLE 44

2,3-Dihydro-5-(phenylmethoxy)cyclopenta[d-]pyrido[1,2-a]-pyrimidin-10(1H)-one, hydrochloride (1:1)

To a solution of 2.92 g. of 2,3-dihydro-5-(phenylmethoxy)cyclopenta[d]pyrido[1,2-a]pyrimidin-10(1H)-one in 25 ml of anhydrous ether, cooled externally by a wet ice bath, is added dropwise and with stirring, 10 ml of a N-ethereal hydrogen chloride solution. The salt separates spontaneously. It is filtered and recrystallized from anhydrous 2-propanol-ether to give the named compound as colorless needles.

EXAMPLE 45

2,3-Dihydro-6-(α,α,α-trifluoro-p-tolyl)cyclopenta[d-]pyrido[1,2-a]pyrimidin-10(1H)-one By substituting 2-amino-4-(α,α,α-trifluoro-p-tolyl)-pyridine (prepared by the procedure of *J. Chem. Soc.*, B, 1292 (1968) from pyridine-N-oxide and p-(α,α,α-trifluoro)toluene diazonium fluoborate) for the 2-amino-3-phenylpyridine in Example 15, there is obtained the named compound as a colorless crystalline compound after recrystallization from cyclohexane.

What is claimed is:
1. A compound of the structure

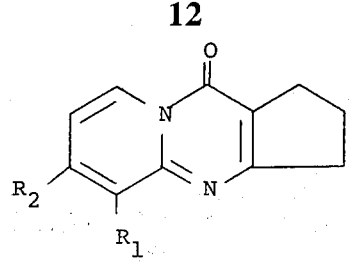

or a pharmaceutically acceptable salt thereof, wherein $R_1$ and $R_2$ are the same or different and are selected from the group consisting of hydrogen, lower alkyl having 1 to 6 carbons, phenyl, phenyl substituted with an alkyl containing 1 to 6 carbons, halo, alkoxy containing 1 to 6 carbons or trifluoromethyl, phenylalkyl the alkyl containing 1 to 6 carbons, halo, hydroxyl, carboxyl, lower alkoxy having 1 to 6 carbons, phenylalkoxy containing 1 to 6 carbons in the alkoxy, carboalkoxy, and carboxamido having the formula R'NHCO wherein R' is hydrogen or lower alkyl having 1 to 6 carbons, one of $R_2$ and $R_1$ being other than hydrogen.

2. The compound as defined in claim 1 wherein $R_1$ and $R_2$ are selected from the group consisting of hydrogen, hydroxyl, alkyl, carboxyl and aralkoxy.

3. The compound as defined in claim 2 wherein $R_2$ is hydrogen and $R_1$ is selected from the group consisting of hydroxyl, alkyl, carboxyl and aralkoxy.

4. The compound as defined in claim 1 wherein one of $R_1$ and $R_2$ is hydrogen.

5. The compound as defined in claim 4 wherein $R_1$ is hydrogen.

6. The compound as defined in claim 4 wherein $R_2$ is hydrogen.

7. The compound as defined in claim 1 having the name 2,3-dihydro-5-hydroxycyclopenta[1,2-d]pyrido[1,2-a]pyrimidin-10(1H)one.

8. The compound as defined in claim 1 having the name 2,3-dihydro-5-(phenylmethoxy)cyclopenta[d-]pyrido[1,2-a]pyrimidin-10(1H)-one.

9. The compound as defined in claim 1 having the name 2,3-dihydro-5-methylcyclopenta[d]pyrido[1,2-a]pyrimidin-10(1H)-one.

10. The compound as defined in claim 1 having the name 1,2,3,10-tetrahydro-10-oxocyclopenta[d-]pyrido[1,2-a]pyrimidine-5-carboxylic acid.

* * * * *

UNITED STATES PATENT AND TRADEMARK OFFICE
CERTIFICATE OF CORRECTION

PATENT NO. : 3,965,100
DATED : June 22, 1976
INVENTOR(S) : Harry L. Yale

It is certified that error appears in the above—identified patent and that said Letters Patent are hereby corrected as shown below:

Title page, line 1 of the title,"[D]" should read --[d]--.
Column 2, line 2, "mixed" should read --fixed--.
Column 3, last structure in the column, on the left side
  of the structure insert --VI--.
Column 7, line 6, "bromopyrimidine" should read
  --bromopyridine--.
Column 7, line 58, "by" should read --By--.

Signed and Sealed this

Twenty-first Day of September 1976

[SEAL]

Attest:

RUTH C. MASON
*Attesting Officer*

C. MARSHALL DANN
*Commissioner of Patents and Trademarks*